United States Patent

Sun et al.

[11] Patent Number: 5,886,207
[45] Date of Patent: Mar. 23, 1999

[54] OPTICALLY ACTIVE COMPOUND OF FLUBROCYTHRINATE, A PROCESS FOR PREPARING THE SAME

[75] Inventors: Guanhe Sun; Weigao Jin; Lin Zuo; Hongyue Xie, all of Shanghai, China

[73] Assignee: Shanghai Zhongxi Pharmaceutical Co. Ltd., Shanghai, China

[21] Appl. No.: 522,321

[22] PCT Filed: Jan. 4, 1995

[86] PCT No.: PCT/CN95/00002

§ 371 Date: Nov. 17, 1995

§ 102(e) Date: Nov. 17, 1995

[87] PCT Pub. No.: WO95/18790

PCT Pub. Date: Jul. 13, 1995

[30] Foreign Application Priority Data

Jan. 5, 1994 [CN] China ................................ 94112002.3

[51] Int. Cl.$^6$ ................................................. C07C 255/41
[52] U.S. Cl. ............................................ 558/354; 514/521
[58] Field of Search .............................. 558/354; 514/521

[56] References Cited

U.S. PATENT DOCUMENTS

| 4,199,595 | 4/1980 | Berkelhammer et al. | 424/304 |
| 4,293,504 | 10/1981 | Suzuki et al. | 558/354 |
| 4,321,212 | 3/1982 | Suzuki et al. | 558/354 |
| 4,503,071 | 3/1985 | Hirano et al. | 558/354 X |
| 4,560,515 | 12/1985 | Stoutamire et al. | 558/354 |
| 4,874,887 | 10/1989 | Jung et al. | 560/124 |

FOREIGN PATENT DOCUMENTS

| 1 034 708 | 8/1989 | China . |
| 1 063 681 | 8/1992 | China . |

OTHER PUBLICATIONS

English translation of Chinese patent 1063681, Aug. 19, 1992.

*Primary Examiner*—Fiona T. Powers
*Attorney, Agent, or Firm*—Merchant, Gould, Smith, Edell, Welter & Schmidt

[57] ABSTRACT

This invention relates to optically active compounds of Flubrocythrinate, their preparations and uses. The insecticidal and miticidal activities of the optically active compounds of the present invention are apparently higher than that of mixture racemic compounds, thus resulting in an increase in rate of utilization as well as a decrease in environmental pollution. Moreover, the process for the preparations of the insecticidal and miticidal agents of the present invention are quite simple, therefore they might have a wide-ranging applications.

2 Claims, No Drawings

OPTICALLY ACTIVE COMPOUND OF FLUBROCYTHRINATE, A PROCESS FOR PREPARING THE SAME

This application is a 371 of PCT/CN95/00002 filed Jan. 4, 1995.

FIELD OF THE INVENTION

The present invention relates to a pyrethroidal pesticide, more particularly, to the Flubrocythrinate optically active compound, their preparations and uses.

BACKGROUND OF THE INVENTION

A new compound of the following structural formula I has been disclosed in Chinese Patent NO. CN 91107318.3 (applicant: Shanghai Zhong Xi Pharmaceutical Co., Ltd.)

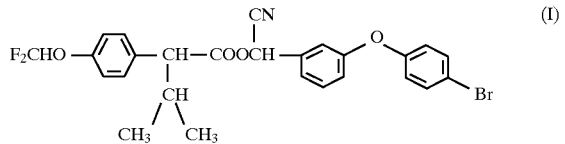

The compound of formula I has the common name Flubrocythrinate, and its chemical name is α-cyano-3-(4-bromophenoxy) benzyl-2-(4-difluoromethoxyphenyl)-3-methylbutyrate.

Flubrocythrinate possesses relatively high insecticidal and miticidal activities and excellent efficacy in comparison with ordinary pyrethroidal pesticides known in prior art, Flubrocythrinate also shows low toxicities towards human and animals and low toxicities towards beneficial insects and animals, in other words, said compound possesses very high insecticidal and miticidal activities and selectivities.

The inventor of the present invention has made efforts in increasing the efficacy and decreasing the dosage of the compound described above. The inventor notes that there are two chiral carbons in the structure formula of compound I, it consists of four optically active isomers. The inventor found, that the efficacy illustrated by an insecticidal and miticidal agents using the racemic form of the compound I as the active ingredient is lower than that using a specific optically active isomer. The dosage of the racemic form of the compound I used is greater than that of a single optically active isomer used, therefore increasing the environmental pollution.

OBJECTION OF THE INVENTION

An aim of the present invention is to provide a powerful insecticidal and miticidal optically active isomeric compound of formula I.

A further objection of the present invention is to provide method for the preparation of some optically active isomers of compound I.

A still further objection of the present invention is to provide applications of said optically active isomers to insecticides and miticides.

SUMMARY OF THE INVENTION

The objections described above are realized on the basis of following conceptions:

The compound Flubrocythrinate possesses four optically active isomers:

1. (S)-α-Cyano-3-(4-bromophenoxy)benzyl-(S)-2-(4-difluoromethoxyphenyl)-3-methylbutyrate (Ia):

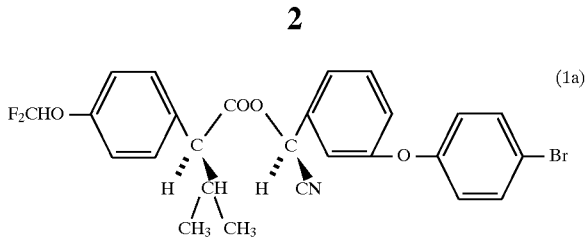

2. (R)-α-Cyano-3-(4-bromophenoxy)benzyl-(S)-2-(4-difluoromethoxyphenyl)-3-methylbutyrate (Ib):

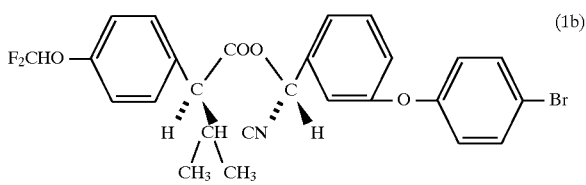

3. (S)-α-Cyano-3-(4-bromophenoxy)benzyl)-(R)-2-(4-difluoromethoxyphenyl)-3-methylbutyrate (Ic):

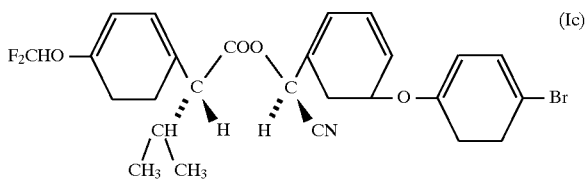

4. (R)-α-Cyano-3-(4-bromophenoxy)benzyl (R)-2-(4-difluoromethoxyphenyl)-3-methylbutyrate (Id):

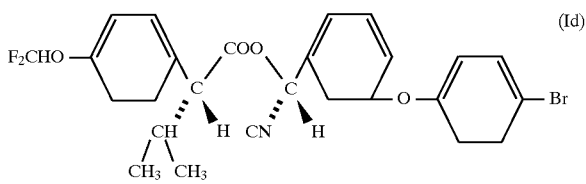

Among these four optically active isomers, the compound Ia, Ib or the racemic mixture of (S,S)-(Ia) and (R,R)-(Id) (this racemic mixture is thereafter referred to A), or the mixture of the isomers thereof possesses apparent pesticidal and miticidal activities:

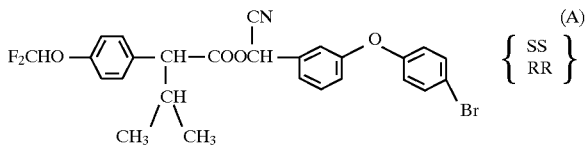

The optically active isomer Ia possesses the strongest pesticidal and insecticidal activities.

The preparative method involved in the present invention includes the following steps:

Reaction equations:

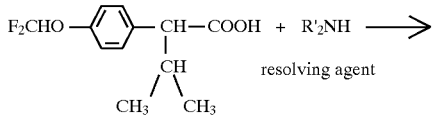

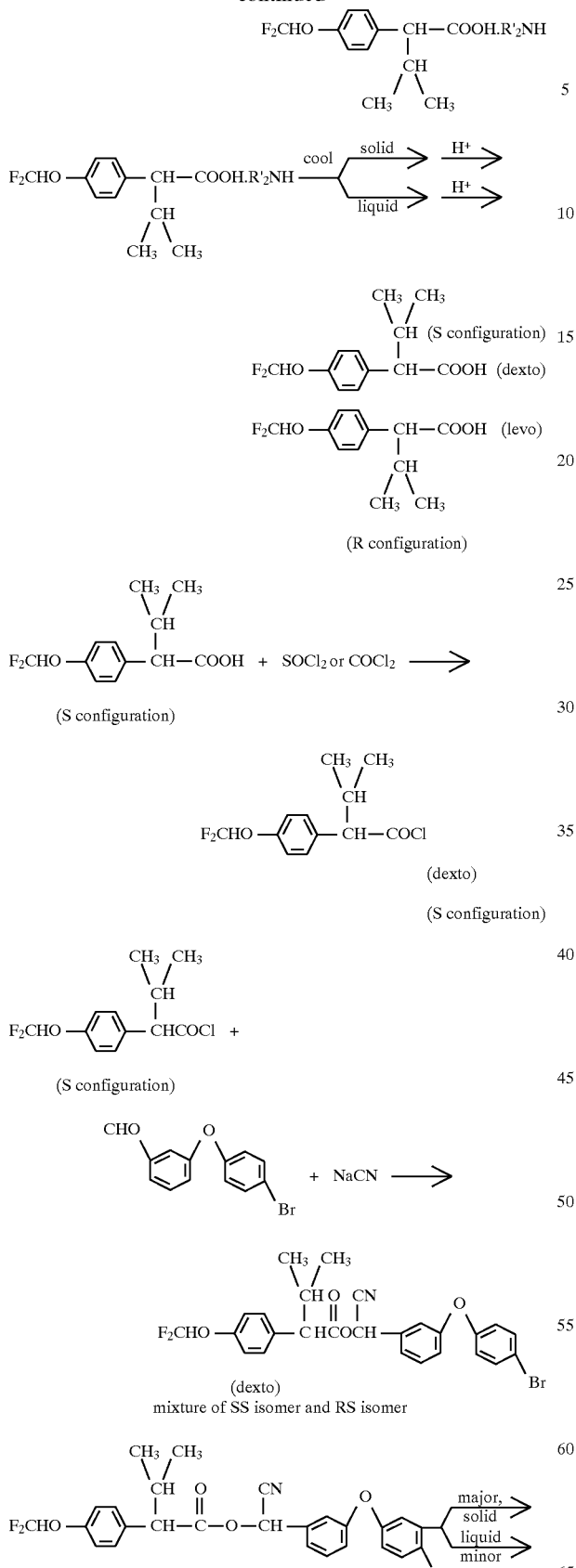
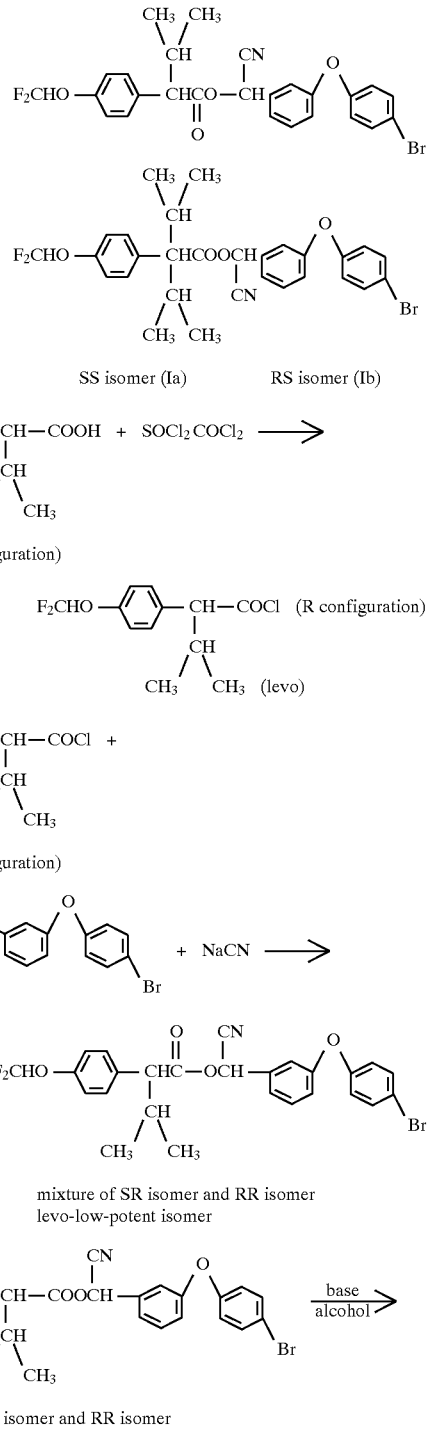
1. Preparation of the compound of formula Ia:
   (1) Preparation of (S)-2-(4-difluoromethoxyphenyl)-3-methylbutyric acid:
   1 part of 2-(4-difluoromethoxyphenyl)-3-methylbutyric acid is dissolved in 1–5 parts (by weight) of solvent comprising an organic solvent such as an aliphatic alcohol, an aromatic hydrocarbon, a keton, a halogenated hydrocarbon, an ether, an ester, or an aliphatic hydrocarbon, etc. After the dissolution is completed, 1–3 moles of resolving agent, an optically active organic base such as 1-(4-nitrophenyl)-2-dimethylamino-1,3-propanediol, quinine, substituted α-aminoethylbenzene and the like, is added. The mixture thus obtained is stirred at −50° C. to 200° C., preferably at 0° C. to reflux temperature of the solvent, for 0.1–100 hours, preferably for 1–10 hours. After the reaction is completed, the reaction mixture is allowed to cool, the solids are then collected by filtration and the filtrate discarded. The solids were added to an aqueous solution of 0.1%–36%, preferably 5%–20%, hydrochloric acid, and heated with stirring at 0° C.–100° C., preferably at 20° C.–50° C., for 0.2–1 hour. Thereafter, the reaction mixture was allowed to cool to room temperature, extracted with organic solvents such as aromatic hydrocarbons, halogenated hydrocarbons, aliphatic hydrocarbons, ethers, ketones, esters and the like, and then remove the solvent in the extract by distillation to give (S)-2-(4-difluoromethoxyphenyl)-3-methylbutyric acid.

(2) Preparation of (S)-2-(4-difluoromethoxyphenyl)-3-methylbutyryl chloride

Add 1–3 moles of thionyl chloride or phosgene into (S)-2-(4-difluoromethoxyphenyl)-3-methylbutyric acid, and allow the mixture to react at 10° C. to reflux temperature of the solvent for 0.1–100 hours, preferably for 1–5 hours. After the reaction is completed, distill off the unreacted thionyl chloride or phosgene to give the (S)-2-(4-difluoromethoxyphenyl)-3-methylbutyryl chloride.

(3) Preparation of a mixture of compounds Ia and Ib 1 mole of (S)-2-(4-difluoromethoxyphenyl)-3-methylbutyryl chloride is added to a mixture containing 1 mole of 3-(4-bromophenoxy) benzaldehyde, 1–3 moles of aqueous NaCN solution and 1–5 times of an organic solvent such as aromatic hydrocarbon, aliphatic hydrocarbon, or ether. The mixture thus obtained is allowed to react at −20°—reflux temperature, preferably at −5° C. to 40° C., for 0.1–100 hours, preferably for 0.5–10 hours. After the reaction is completed, the reaction mixture is extracted with a solvent such as aromatic hydrocarbon, aliphatic hydrocarbon, ether, ester, halogenated hydrocarbon and the like, the extract is then distilled to remove the solvent and a mixture of compounds Ia and Ib is obtained.

(4) Preparation of the compound of formula Ia

A mixture of compounds Ia and Ib is dissolved in its 1–5 times of amounts of solvent such as lower molecular weight alcohol, aliphatic hydrocarbon, or ketone. This solution is added 0.01–3 moles of a base such as an organic tertiary amine triethylamine, dimethylaniline and the like, or an organic base such as pyridine, and an inorganic base such as sodium carbonate, sodium bicarbonate and the like. The mixture was allowed to react at −40° C. to 50° C., preferably at −10° C. to 10° C., for 1–100 hours, preferably for 3–15 hours. After the reaction is completed, allow the reaction mixture to stand and collect by filtering the crystals which precipitate upon standing to give Ia.

2. Preparation of A

Compound I is added to a mixture of 0.01–3 moles of base and alcohol, the said base includes an organic base such as triethylamine, pyridine, or an inorganic base such as sodium carbonate, sodium bicarbonate and the like, while the said alcohol includes a lower molecular weight alcohol such as methanol, ethanol, isopropanol and the like. After the dissolution is completed, the mixture is stirred at −40° C. to reflux temperature, preferably at −10° C. to 10° C., for 1–100 hours, preferably for 5–20 hours. The mixture is allowed to stand after the reaction is completed, and the crystals are collected upon precipitation by filtration to give A.

The present invention further relates to the use of said optically active isomers as insecticidal and miticidal agents. They are characterized in comprising 0.1–99.9% (by weight) of said optically active isomers or the mixtures thereof as the active ingredient and 99.9–0.1% (by weight) of pesticidally acceptable carriers. The insecticidal and miticidal agents thus obtained exhibit high potent activity against harmful mites such as mite of cotton leaf (*tetranychus telarius Linnaeus*), Haw red spider mite (*Tetranychus viennensis zacher*) and the like, aphids such as cabbage aphid (*Brevicoryne brassicae*), wheat aphid, turnip aphid (*Rhopalosiphum pseudobrassicae Davis*) and the like, and lepidoptera harmful insects such as bollworm (*Heliothis armigera*), pink bollworm (*Pectinophora gossypiella*), diamond back moth (*Plutella maculipennis* Curtis) and the like, and also exhibit good effect against borers such as carposina nipponensis walsingham and the like. They can be applied to cotton plant, vegetables, fruit trees, and other economic crops for killing harmful insects.

The carriers described above are those pesticidally acceptable carriers, including, for example, the solvents such as alkanes and alcohols, the emulsifiers such as suspending agent, anionic, cationic, or non-ionic emulsifier, and the solid diluent such as kaolin and silica.

The said insecticidal and miticidal agents may be in the form of an emulsifiable concentrate, a suspension concentrate, a granules, or a dust and the like.

Formulation of an insecticidal and miticidal emulsifiable concentrate containing compound Ia or A as the active ingredient:

Mix under stirring the compound Ia or A with a solvent such as alkane, aromatic alkane, or aliphatic alkane in a proportion of 0.1%–99.9% to 99.9%–0.1% (by weight). After dissolution, add an emulsifier such as anionic, cationic or non-ionic emulsifier and mix thoroughly, and then stir the mixture at a temperature range of 0° C.–100° C., preferably at 20° C.–60° C. for 0.5–2 hours. An emulsifiable oil containing 0.1%–99.9% of compound Ia or A is obtained.

Formulation of an insecticidal and miticidal water dispersible granules (WG) containing compound Ia or A as the active ingredient:

Stir and heat at 50° C.–120° C. a mixture of compound Ia or A (in a proportion of 1%–90% by weight) and a solid diluent (in a proportion of 99%–10% by weight) such as bentonite, kaolinite, silica to a fused state so as to obtain a mother substance which is then blended, after to room temperature, with adjuvants (in a proportion of 99%–10% by weight) such as a wetter, a dispersing agent, a surface active agent such as powder of Chinese honey locust, cake of tea-seeds, synthetic alkylphenyl sulfonate, phenylethylene phenyl polyoxyethylene ether, anionic emulsifier, cationic emulsifier, non-ionic emulsifier. Crush the initial mixture thus formed through a grinder, such as hammer mill, airstream mill, and then mix the resulting material for 1–2 hours. The homogeneous material thus obtained is granulated into granules having a diameter of 300–1700 μm, and then dried at 40° C.–80° C. to give a water dispersible granules (WG) containing compound Ia or A.

Formulation of an insecticidal and miticidal suspension concentrate (SC) containing compound Ia or A as the active ingredient:

Heat at 80° C.–140° C. a mixture of compound Ia or A (in a proportion of 1%–70 % by weight) and a hydrophilic solvent (in a proportion of 10%–50% by weight) such as ethylene glycol, ethylene glycol dialkyl ether, diethylene glycol mono alkyl ether, glycerine, and lower alcohol until a solution is obtained. Add to this solution a non-ionic surface active agent, anionic surface active agent (in a proportion of 10%–50% by weight) such as polyethylene oxide condensates of higher aliphatic alcohol-, mono- or dialkylphenol-, higher aliphatic carboxylic acid, and ammonium laurylphenyl sulfonate, followed by addition of polymeric dispersing agent such as polyvinyl alcohol, carboxymethyl cellulose, sodium alginate, gum acacia, and antifreezer, antifoamer. The mixture thus obtained is then treated at 25° C.–50° C. with added deionized water in a sand mill or ultramicro mill, and kept at that temperature under vigorous stirring for 3 hours to produce a suspension concentrate (SC) containing compound Ia or A.

Formulation of an insecticidal and miticidal dustable powder (DP) containing compound Ia or A as the active ingredient:

Stir and heat at 50° C.–120° C. a mixture of compound Ia or A (in a proportion of 1%–90% by weight) and a solid dilute (in a proportion of 99%–10% by weight) such as bentonite, kaolinite, silica to a fused state so as to obtain a mother substance which is then blended, after being cooled to room temperature, with adjuvants (in a proportion of 99%–10% by weight) such as a wetter, a dispersing agent, a surface active agent such as powder of Chinese honey locust, cake of tea-seeds, synthetic alkylphenyl sulfonate, phenylethylene phenyl polyoxyethylene ether, anionic emulsifier, cationic emulsifier, non-ionic emulsifier. Crush the initial mixture thus obtained through a grinder, and control the size of particles thus obtained in a range of 70–200 μm. The resulting powder is further mixed for 1–2 hours to give a dustable powder (DP) containing compound Ia or A.

Formulation of an insecticidal and miticidal wettable powder (WP) containing compound Ia or A as the active ingredient:

Stir and heat at 50° C.–120° C. a mixture of compound Ia or A (in a proportion of 1%–90% by weight) and a solid diluent (in a proportion of 99%–10% by weight) such as bentonite, kaolinite, silica to a fused state so as to obtain a mother substance which is then blended, after being cooled to room temperature, with adjuvants (in a proportion of 99%–10% by weight) such as a wetter, a dispersing agent, a surface active agent such as powder of Chinese honey locust, cake of tea-seeds, synthetic alkylphenyl sulfonate, phenylethylene phenyl polyoxyethylene ether, anionic emulsifier, cationic emulsifier, non-ionic emulsifier. Crush the initial mixture thus obtained through a grinder, such as hammer mill, airstream mill, and then mix the resulting material for 1–2 hours to give a wettable powder containing compound Ia or A in a proportion of 1%–90% by weight.

The present invention will be further described with reference to the following examples, but it should be construed that the present invention is in no way limited to these examples.

PREFERRED EXAMPLES

Example 1

Preparation of (S)-2-(4-difluoromethoxyphenyl)-3-methylbutyric acid

Dissolve 50 g (0.2 mole) of 2-(4-difluoromethoxyphenyl)-3-methylbutyric acid in 150 g of ethyl alcohol and to this solution is added 0.2 mol of resolving agent 1-(4-nitrophenyl)-2-dimethylamino-1,3-propanediol. Heat the solution with stirring under reflux for 8 hours, then cool, filter, and transfer the resulting solids to 73 g of 10% hydrochloric acid. Heat the mixture with stirring at 30° C. for 2 hours and then allow the mixture to cool to room temperature. The resulting mixture is extracted with benzene 2–3 times, and the solvent benzene is then removed by distillation to give 21 g (yield: 42%) of (S)-2-(4-difluoromethoxyphenyl)-3-methylbutyric acid.

Example 2

Preparation of (S)-2-(4-difluoromethoxyphenyl)-3-methylbutyric acid

Dissolve 50 g of 2-(4-difluoromethoxyphenyl)-3-methylbutyric acid in 150 g of ethyl alcohol and to this solution is added 0.24 mole of resolving agent 1-(4-nitrophenyl)-2-dimethylamino-1,3-propanediol. Heat the solution with stirring under reflux for 1.5 hours, then cool, filter, and transfer the resulting solids to 73 g of 10% hydrochloric acid. Heat the mixture with stirring at 30° C. for 2 hours and then allow the mixture to cool to room temperature. The resulting mixture is extracted with benzene 2–3 times, and the solvent benzene is then removed by distillation to give 21.25 g (yield: 42.5%) of (S)-2-(4-difluoromethoxyphenyl)-3-methylbutyric acid.

Example 3

Preparation of (S)-2-(4-difluoromethoxyphenyl)-3-methylbutyric acid

Dissolve 50 g of 2-(4-(difluoromethoxyphenyl)-3-methylbutyric acid in 130 g of toluene and to this solution is added 0.22 mole of resolving agent 1-(4-nitrophenyl)-2-dimethylamino-1,3-propanediol. Heat the solution with stirring under reflux for 6 hours, then cool, filter, and transfer the resulting solids to 73 g of 10% hydrochloric acid. Heat the mixture with stirring at 30° C. for 2 hours and then allow the mixture to cool to room temperature. The resulting mixture is extracted with benzene 2–3 times, and the solvent benzene is then removed by distillation to give 21.5 g (yield: 43%) of (S)-2-(4-difluoromethoxyphenyl)-3-methylbutyric acid.

Example 4

Preparation of (S)-2-(4-difluoromethoxyphenyl)-3-methylbutyric acid

Dissolve 50 g of 2-(4-difluoromethoxyphenyl)-3-methylbutyric acid in 130 g of toluene and to this solution is added 0.24 mole of resolving agent 1-(4-nitrophenyl)-2-dimethylamino-1,3-propanediol. Heat the solution with stirring under reflux for 6 hours, then cool, filter, and transfer the resulting solids to 48.7 g of 15% hydrochloric acid. Heat the mixture with stirring at 40° C. for 2 hours and then allow the mixture to cool to room temperature. The resulting mixture is extracted with benzene 2–3 times, and the solvent benzene is then removed by distillation to give 21.75 g (yield: 43.5%) of (S)-2-(4-difluoromethoxyphenyl)-3-methylbutyric acid.

Example 5

Preparation of (S)-2-(4-difluoromethoxyphenyl)-3-methylbutyric acid

Dissolve 50 g of 2-(4-difluoromethoxyphenyl)-3-methylbutyric acid in 130 g of toluene and to this solution is added 0.24 mole of resolving agent quinine. Heat the solution with stirring under reflux for 6 hours, then cool, filter, and transfer the resulting solids to 49 g of 15% hydrochloric acid. Heat the mixture with stirring at 40° C. for 2 hours and then allow the mixture to cool to room temperature. The resulting mixture is extracted with benzene 2–3 times, and the solvent benzene is then removed by distillation to give 21 g (yield: 42%) of (S)-2-(4-difluoromethoxyphenyl)-3-methylbutyric acid. $[\alpha]_D^{RT}=(+)$ 40.5 (c=1.356 g/100 ml, CHCl$_2$)

Example 6
Preparation of (S)-2-(4-difluoromethoxyphenyl)-3-methylbutyryl chloride Add 32.8 g (0.275 mole) of thionyl chloride to 42 g (0.17 mole) of the obtained (S)-2-(4-difluoromethoxyphenyl)-3-methylbutyric acid, heat with stirring under reflux for 4 hours, and then distill off the unreacted thionyl chloride to give 43 g of (S)-2-(4-difluoromethoxyphenyl)-3-methylbutyryl chloride.

Example 7
Preparation of (S)-2-(4-difluoromethoxyphenyl)-3-methylbutyryl chloride Add 32.8 g (0.275 mole) of thionyl chloride to 42 g (0.17 mole) of the obtained (S)-2-(4-difluoromethoxyphenyl)-3-methylbutyric acid, heat with stirring under reflux for 1 hour, and then distill off the unreacted thionyl chloride to give 41 g of (S)-2-(4-difluoromethoxyphenyl)-3-methylbutyryl chloride.

Example 8
Preparation of (S)-2-(4-difluoromethoxyphenyl)-3-methylbutyryl chloride Add 32.8 g (0.275 mole) of thionyl chloride to 42 g (0.17 mole) of the obtained (S)-2-(4-difluoromethoxyphenyl)-3-methylbutyric acid, heat with stirring under reflux for 2 hours, and then distill off the unreacted thionyl chloride to give 42.5 g of (S)-2-(4-difluoromethoxyphenyl)-3-methylbutyryl chloride.

Example 9
Preparation of (S)-2-(4-difluoromethoxyphenyl)-3-methylbutyryl chloride Add 32.8 g (0.275 mole) of thionyl chloride to 42 g (0.17 mole) of the obtained (S)-2-(4-difluoromethoxyphenyl)-3-methylbutyric acid, heat with stirring under reflux for 8 hours, and then distill off the unreacted thionyl chloride to give 42.5 g of (S)-2-(4-difluoromethoxyphenyl)-3-methylbutyryl chloride.

Example 10
Preparation of a mixture of optically active compound Ia and Ib

Add 43 g (0.16 mole) of (S)-2-(4-difluoromethoxyphenyl)-3-methylbutyryl chloride to a mixture of 45 g (0.16 mole) of 3-(4-bromophenoxy)benzaldehyde, 25 g of aqueous NaCN solution and 32 ml of diethyl ether, and the mixture thus obtained is then heated under reflux with stirring for 6 hours. Allow the mixture to cool to room temperature and extract 2–3 times with benzene. Benzene is then distilled off by distillation to give 78 g of a mixture of compound Ia and Ib.

Example 11
Preparation of a mixture of optically active compound Ia and Ib

Add 43 g (0.16 mole) of (S)-2-(4-difluoromethoxyphenyl)-3-methylbutyryl chloride to a mixture of 45 g (0.16 mole) of 3-(4-bromophenoxy)benzaldehyde, 25 g of aqueous NaCN solution and 35 ml of toluene, and the mixture thus obtained is then heated under reflux with stirring for 6 hours. Allow the mixture to cool to room temperature and extract 2–3 times with benzene. Benzene is then distilled off by distillation to give 76 g of a mixture of compound Ia and Ib.

Example 12
Preparation of a mixture of optically active compound Ia and Ib

Add 43 g of (S)-2-(4-difluoromethoxyphenyl)-3-methylbutyryl chloride to a mixture of 45 g of 3-(4-bromophenoxy)benzaldehyde, 25 g of aqueous NaCN solution and 130 ml of diethyl ether, and the mixture thus obtained is then heated under reflux with stirring for 1 hour. Allow the mixture to cool to room temperature and extract 2–3 times with benzene. Benzene is then distilled off by distillation to give 75 g of a mixture of compound Ia and Ib.

Example 13
Preparation of a mixture of optically active compound Ia and Ib

Add 43 g of (S)-2-(4-difluoromethoxyphenyl)-3-methylbutyryl chloride to a mixture of 45 g of 3-(4-bromophenoxy)benzaldehyde, 25 g of aqueous NaCN solution and 130 ml of diethyl ether, and the mixture thus obtained is then heated under reflux with stirring for 12 hours. Allow the mixture to cool to room temperature and extract 2–3 times with benzene. Benzene is then distilled off by distillation to give 78 g of a mixture of compound Ia and Ib.

Example 14
Preparation of optically active compound Ia

Dissolve 78 g of a mixture of Ia and Ib in a solvent consisting of 15.6 g of triethylamine and 140.4 g of ethanol, stir to dissolve the solids and allow to react at 0° C. for 5 hours, then add seed crystals of compound Ia to the reaction mixture to cause the crystallization. The crystals formed are collected by filtration and dried to give 65.5 g of Ia.

MS(M/Z): 531(M$^+$2), 529(M$^+$),

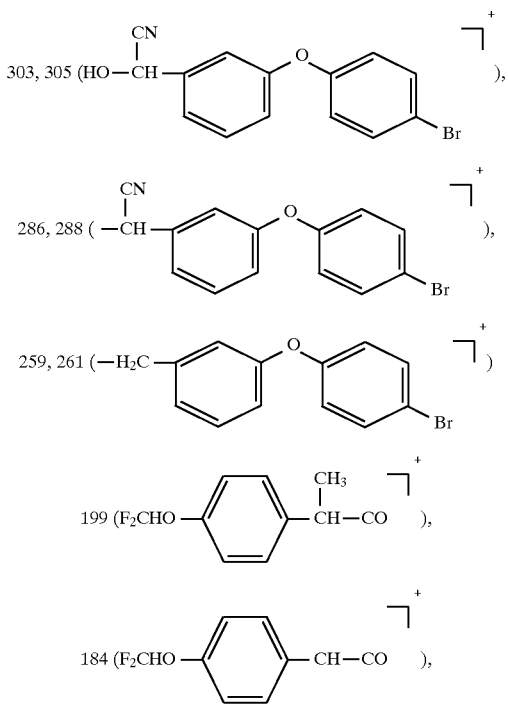

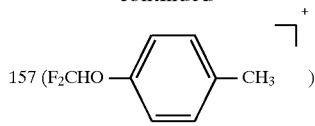

Example 15
Preparation of optically active compound Ia

Dissolve 78 g of a mixture of Ia and Ib in a solvent consisting of 15.6 g of triethylamine and 140.4 g of ethanol, stir to dissolve the solids and allow to react at 5° C. for 5 hours, then add seed crystals of compound Ia to the reaction mixture to cause the crystallization. The crystals formed are collected by filtration and are then dried to give 66 g of Ia.

NMR: 0.71(3H), 1.01(3H), 2.32(1H), 3.23(1H), 6.28(1H), 6.85–7.46(13H).

Example 16
Preparation of optically active compound Ia

Dissolve 78 g of a mixture of compound Ia and Ib in a solvent consisting of 15.6 g of triethylamine and 140.4 g of ethanol, stir to dissolve the solids and allow to react at 20° C. for 5 hours, then cool it slowly to 2° C. followed by addition of seed crystals of compound Ia to cause the crystallization to occur. The crystals formed are collected by filtration and are then dried to give 64 g of Ia.

IR: 2250($v_{C-N}$), 1702 ($v_{C-D}$), 1250($v_{C-O}$), 830,788 ($v_{\phi-H}$), 500 ($v_{\phi-Br}$).

NMR: 0.71(3H), 1.01(3H), 2.32 (1H), 3.32 (1H), 6.28 (1H), 6.85–7.46(13H)

MS(M/Z): 529,531(M$^+$, M$^+$+2),

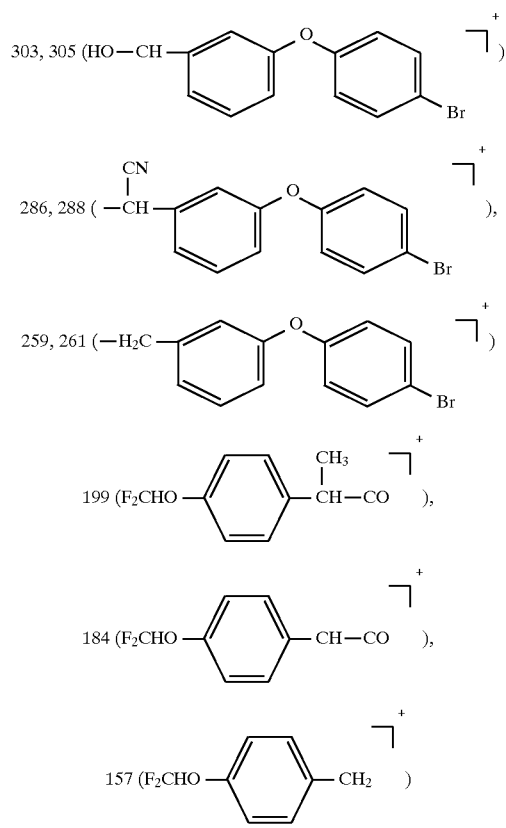

Example 17
Preparation of optically active compound Ia

Dissolve 78 g of a mixture of Ia and Ib in a solvent consisting of 15.6 g of triethylamine and 140.4 g of ethanol, stir to dissolve the solids and allow to react at 10° C. for 10 hours, then cool it slowly to 2° C. and add seed crystals of compound Ia to the reaction mixture to cause the crystallization. The crystals formed are then collected by filtration and dried to give 65.5 g of compound Ia.

The data of IR, NMR and MS are the same as that in Example 16.

Example 18
Preparation of optically active compound Ia

Dissolve 78 g of a mixture of Ia and Ib in a solvent consisting of 15.6 g of triethylamine and 140.4 g of ethanol, stir to dissolve the solids and allow to react at 10° C. for 20 hours, then cool it slowly to 2° C. and add seed crystals of compound Ia to the reaction mixture to cause the crystallization. The crystals formed are then collected by filtration and dried to give 65 g of compound Ia.

$[\alpha]_D^{RT}=(-)2.73°$ (absolute alcohol, c=1.87 g/100 ml)

The data of IR, NMR and MS is same as that in Example 16.

Example 19
Preparation of optically active compound Ia

Dissolve 78 g of a mixture of Ia and Ib in a solvent consisting of 9 g of acetone and 280 g of pyridine, stir to dissolve the solids and allow to react at 10° C. for 10 hours, then cool it slowly to 2° C. and add seed crystals of compound Ia to the reaction mixture to cause the crystallization. The crystals formed are collected by filtration and dried to give 63 g of compound Ia The data of IR, NMR and MS is the same as above.

Example 20
Preparation of racemic high-potent A

Add 25 g of compound I to a mixture of 5 g of triethylamine and 45 g of ethanol under stirring. After the dissolution of the solids is completed, allow the reactants to react at 10° C. for 6 hours. Cool the mixture slowly to 8° C., and then add seed crystals of A to cause the crystallization. The crystals formed are collected by filtration and dried to give 19 g of A.

IR: 2250($v_{C-N}$),1702 ($v_{C-D}$), 1250($v_{C-O}$), 830,788 ($v_{\phi-H}$), 500 ($v_{\phi-Br}$).

Example 21
Preparation of racemic high-potent A

Add 25 g of compound I to a mixture of 5 g of triethylamine and 45 g of ethanol under stirring. After the dissolution of the solids is completed, allow the reactants to react at 10° C. for 15 hours. Cool the mixture slowly to 8° C., and then add seed crystals of A to cause the crystallization. The crystals formed are collected by filtration and dried to give 20 g of A.

NMR: 0.71 (3H), 1.01 (3H), 2.32 (1H), 3.23 (1H), 6.28 (1H), 6.85–7.46 (13H)

Example 22
Preparation of racemic high-potent A

Add 25 g of compound I to a mixture of 5 g of triethylamine and 45 g of ethanol under stirring. After the dissolution of the solids is completed, allow the reactants to react at 10° C. for 20 hours. Cool the mixture slowly to 8° C., and then add seed crystals of A to cause the crystallization. The crystals formed are collected by filtration and dried to give 20.5 g of A.

IR: 2250 ($v_{C-N}$), 1702 ($v_{C-O}$), 1250 ($v_{C-O}$), 830,788 ($v_{\phi-H}$), 500 ($v_{\phi-Br}$).

Example 23
Preparation of racemic high-potent A

Add 25 g of compound I to a mixture of 5 g of triethylamine and 45 g of ethanol under stirring. After the dissolution of the solids is completed, allow the reactants to react at 10° C. for 4 hours. Cool the mixture slowly to 8° C., and then add seed crystals of A to cause the crystallization. The crystals formed are collected by filtration and dried to give 17 g of A.

The data of IR, NMR and MS is the same as above.

Example 24
Preparation of racemic high-potent A

Add 25 g of compound I to a mixture of 4 g of pyridine and 50 g of isopropanol under stirring. After the dissolution of the solids is completed, allow the reactants to react at 10° C. for 6 hours. Cool the mixture slowly to 8° C., and then add seed crystals of A to cause the crystallization. The crystals formed are collected by filtration and dried to give 17.5 g of A.

The data of IR, NMR and MS is the same as above.

Example 25
Formulation of an emulsifiable concentrate of Ia

In a reactor, equipped with a stirrer, place 6.25 g of compound Ia, 8 g of ethanolamine and 85.75 g of toluene, and the mixture is stirred. The mixture is heated at 50° C. under stirring for 1 hour to produce an emulsified oil containing 6.25% of Ia.

Example 26
Formulation of an emulsifiable concentrate of Ia

In a reactor, equipped with a stirrer, place 25 g of compound Ia, 15 g of ethanolamine and 60 g of xylene, and the mixture is stirred. The mixture is heated at 40° C. under stirring for 2 hours to produce an emulsifiable concentrate containing 25% of Ia.

Example 27
Formulation of an emulsifiable concentrate of A

In a reactor, equipped with a stirrer, place 62.5 g of A, 20 g of toluenesulfonate and 17.5 g of ethanol, and the mixture is stirred. The mixture is heated at 50° C. under stirring for 2 hours, yielding an emulsifiable concentrate containing 62.5% of A.

Example 28
Formulation of an emulsifiable concentrate of A

In a reactor, equipped with a stirrer, place 12.5 g of A, 10 g of ethyl phenol polyethylene ether and 77.5 g of cyclohexane. The mixture is heated at 30° C. under stirring for 1 hour, yielding an emulsifiable concentrate containing 12.5% of A.

Example 29
Formulation of a suspension concentrate of compound Ia or A

A mixture of 20 g of compound Ia or A and 15 g of ethylene glycol is heated at 95° C. until a solution is obtained, followed by dissolving in 12 g of nonylphenoxy polyethylene glycol sulfate and 6 g of sodium lauryl phenyl sulfonate, 4 g of urea, 2 g of silicon, and 2 g of carbomethoxy cellulose. The mixture thus obtained is then stirred in a sand grinder with 39 g of deionized water at 35° C., and kept at that temperature under vigorous stirring for 3 hours and control the size of particles thus obtained below 5 μm, yielding a suspension concentrate (SC) containing 20% of compound Ia or A.

Example 30
Formulation of a water dispersible granule (WG) containing compound Ia or A A mixture of 20 g of compound Ia or A and 52 g of bentonite is heated with stirring at about 90° C. for 0.5–1 hour. The mixture is then blended, after being cooled to room temperature, with 18 g of anionic emulsifier, non-ionic emulsifier, and 13 g of dispersing agent. The initial mixture thus obtained is crushed through a grinder and then mixed for 1–2 hours. The homogeneous material thus formed is granulated in a granulator into granules having a diameter of 300–1700 μm, and then dried to about 50° C. to give a water dispersible granule (WG) containing 20% of compound Ia or A.

Example 31
Formulation of a wettable powder (WP) containing compound Ia or A A mixture of 10 g of compound Ia or A and 70 g of kaolinite is heated with stirring at 90° C. for 1 hour. The mixture is then blended, after being cooled to room temperature, with 10 g of alkylphenylene sulfonate, 5 g of dispersing agent, and 5 g of powder of Chinese honey locust. The initial mixture thus obtained is crushed through an airsteam mill and then mixed for 1.5 hours to give a wettable powder (WP) containing 10% of compound Ia or A.

Example 32
Formulation of a dustable powder (DP) containing compound Ia or A A mixture of 25.6 g of compound Ia or A and 46.4 g of silica is heated with stirring at about 70° C. for 0.5–1 hour. The mixture is then blended, after being cooled to room temperature, with 15 g of phenylethylene phenyl polyoxyethylene ether, 8 g of fatty acid amide adjuvant, and 5 g of dispersing agent. The initial mixture thus obtained is crushed through a mill and the size of the crushed powder is controlled in a range of 70–200 μm and then mix the resulting powder for further 1–2 hours to give a dustable powder (DP) containing 25.6% of compound Ia or A.

TEST PROCEDURE

1. Laboratory toxicity test against tetranychus telarius Linnaeus (1) Method of manipulation: (Pasting Method)

Take the robust mature female mites, and paste the back of the mite on a piece of glass with a transparent adhesive tape. Every piece of glass pasted with 40 mites, and three pieces of glasses for each concentration, each insecticide repeated three times at five concentration. The glasses pasted with the mites are inspected under a binocular disseceteined microscope, reject the inactive one and record the number of the qualified mites. Immerse the above glasses in a insecticidal solution of specified concentration for 5 seconds and take out from the solution. Use a piece of absorbent paper to absorb the surplus insecticidal solution, transfer the above treated glasses to a culture dish previously fitted with a wetted cotton wool. The culture dish is kept in a thermostat oven at 28° C. for 48 hours, and inspect the number of dead mites under binocular dissecteined microscope. Standard for death judgement: use a needle to move the body of the mite, wholly inflexible judged as death.

(2) Results

TABLE 1

| Various optically active isomer (hour) | $LC_{50}$ (ppm) | $LC_{90}$ (ppm) | time |
|---|---|---|---|
| Ia | 4 | 52 | 24 |
| A | 10 | 110 | 24 |
| compound (I) | 19 | 232 | 24 |
| Ib | 12 | 130 | 24 |
| Ic | 220 | 2580 | 24 |
| B | 180 | 2100 | 24 |
| Id | 1200 | 8000 | 24 |

2. Laboratory toxicity test against wheat aphid
  (1) Method of manipulation (Topic application method)
    Weigh third instar larva on a swift electronic balance to obtain 8–18 mg/larva, and 0.083 μl of the insecticide solution in acetone at specified concentration with a microsyringe to the dorsal thorax of the larva, and then transfer the larva into a finger-type tube charged with artificial fodder, each tube for one larva, each concentration for 30 tubes, each insecticide run at 5 concentrations, and repeat 3 times. Place the tubes in a thermostat oven at 27° C. for 48 hours, and inspect the number of dead larva. Standard for death judgement: judge the wholly inflexible test aphid as death.
  (2) Results

TABLE 2

| various active compound | $LD_{50}$ (μg/larva) |
|---|---|
| Ia | 0.0001783 |
| A | 0.0003712 |
| compound I | 0.0007247 |
| Ib | 0.0003850 |
| Ic | 0.009252 |
| B | 0.008430 |
| Id | 0.05047 |

The results illustrated in Tables 1 and 2 show that compound Ia is 4.46 times as toxic as compound I against tetranychus telarius Linnaeus and is 4.06 times as toxic as compound I against wheat aphid. The compound A and Ib are 2.11 times and 1.78 times as toxic as compound I against tetranychus telarius Linnaeus, and are 1.95 times and 1.88 times as toxic as compound I against wheat aphid respectively. Therefore compound Ia has the preferred effect, and the dosage needed is the lowest; the next one are A and compound Ib. Thus, the efficacy of the optically active isomer of compound Ia, Ib or racemic compound A is apparently better than compound I, and the dosage of the said compound Ia, Ib or racemic compound A is lower than that of compound I, therefore they can most efficiently be used for insecticidal and miticidal purpose.

The process for the preparation of the insecticidal and miticidal agent of the present invention is quite simple, thus the process described herein is suitable for a large scale production, and also is advantageous to the decrease in using compound I as insecticides, that is to say, is advantageous to an increase in the rate of utilization as well as a decrease in environmental pollution. Therefore, it may be expected that the said insecticides can be widely used in agricultural crops for the control of harmful insects.

What is claimed is:

1. A process for preparing an optically active isomeric compound Flubrocythrinate of the formula Ia
  (S)-α-Cyano-3-(4-bromophenoxy) benzyl-(S)-2-(4-difluoromethoxyphenyl)-3-methlbutyrate Ia:

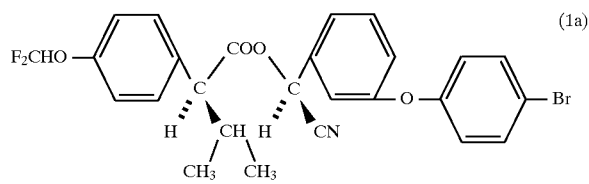

which comprises of steps of:
  (a) preparing a compound of formula Ia by:
    1. preparing (S)-2-(4-difluoromethoxyphenyl)-3-methyltuyric acid by:
      (a) dissolving 2-(4-Difluoromethoxyphenyl-3-methylbutyric acid in 1 to 5 times by weight organic solvent,
      (b) after dissolution, adding 1 to 3 moles of optically active organic base,
      (c) stirring the resulting mixture at −50° C. to 200° C. for 0.1 to 100 hours,
      (d) separating the solids by filtration,
      (e) adding 0.1 to 36% hydrochloric acid to said solids and stirring the solids and hydrochloric acid at 0° C. to 100° C. for 0.2 to 1 hour, and
      (f) separating the (S)-2-(4-difluoromethoxyphenyl)-3-methylbutyric acid;
    2. preparing (S)-2-(4-difluoromethoxyphenyl)-3-methylbutyryl chloride by:
      (a) adding 1 to 3 moles of thionyl chloride or bubbled phosgene into said (S)-2-(4-difluoromethoxyphenyl)-3-methylbutyric acid, and
      (b) reacting the mixture of step 2(a) at 10° C. to the refluxing temperature of the solvent of step 2(a) for 0.1 to 100 hours to produce (S)-2-(4-difluoromethoxyphenyl)-3-methylbutyryl chloride;
    3. preparing a mixture of compounds Ia and Ib (R)-α-Cyano-3-(4-bromophenoxy) benzyl-(S)-2-(4-difluoromethoxyphenyl)-3-methlbutyrate Ib:

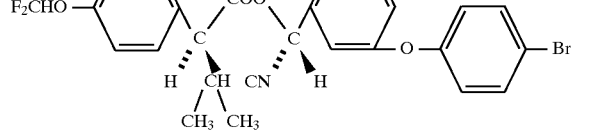

by:
      (a) adding 1 mole of (S)-2-(4-difluoromethoxyphenyl)-3-methylbutyryl chloride to a mixture of 1 mole of 3-(4-bromophenoxy)benzaldehyde, 1 to 3 moles of aqueous NaCN and 1 to 5 times by weight organic solvent,
      (b) reacting the mixture of step 3(a) at −20° C. to the reflux temperature of the solvent in the mixture of step 3(a) for 0.1 to 100 hours, and
      (c) separating compounds Ia and Ib from the mixture of step 3(b); and
    4. preparing compound Ia by:
      (a) dissolving the mixture of compounds Ia and Ib obtained in step 3(c) in 1 to 5 times by weight of a solvent selected from the group consisting of a lower molecular weight alcohol, an aliphatic hydrocarbon, a ketone, and mixtures thereof,
      (b) adding the solution of step 4(a) to 0.01 to 3 moles of a base, (c) reacting the mixture of step 4(b) at −40° C. to 50° C. for 1 to 100 hours, and (d) collecting the precipitate by filtration to give compound Ia.

2. A process for the preparation of a racemic mixture comprising the compound of formula Ia (S)-α-Cyano-3-(4-bromophenoxy) benzyl-(S)-2-(4-difluoromethoxyphenyl)-3-methlbutyrate Ia:

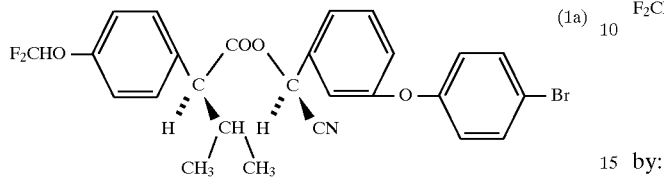

and the compound of formula Id (R)-α-Cyano-3-(4-bromophenoxy) benzyl-(R)-2-(4-difluoromethoxyphenyl)-3-methlbutyrate Id:

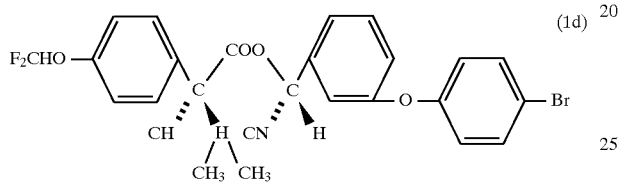

comprising the steps of:

(a) preparing the compound of formula Ia by:

1. preparing (S)-2-(4-difluoromethoxyphenyl)-3-methyltuyric acid by:

(a) dissolving 2-(4-Difluoromethoxyphenyl-3-methylbutyric acid in 1 to 5 times by weight organic solvent, (b) after dissolution, adding 1 to 3 moles of optically active organic base, (c) stirring the resulting mixture at −50° C. to 200° C. for 0.1 to 100 hours, (d) separating the solids by filtration, (e) adding 0.1 to 36% hydrochloric acid to said solids and stirring the solids and hydrochloric acid at 0° C. to 100° C. for 0.2 to 1 hour, and (f) separating the (S)-2-(4-difluoromethoxyphenyl)-3-methylbutyric acid;

2. preparing (S)-2-(4-difluoromethoxyphenyl)-3-methylbutyryl chloride by:

(a) adding 1 to 3 moles of thionyl chloride or bubbled phosgene into said (S)-2-(4-difluoromethoxyphenyl)-3-methylbutyric acid, and (b) reacting the mixture of step 2(a) at 10° C. to the refluxing temperature of the solvent of step 2(a) for 0.1 to 100 hours to produce (S)-2-(4-difluoromethoxyphenyl)-3-methylbutyryl chloride;

3. preparing a mixture of compounds Ia and Ib (R)-α-Cyano-3-(4-bromophenoxy) benzyl-(S)-2-(4-difluoromethoxyphenyl)-3-methlbutyrate Ib:

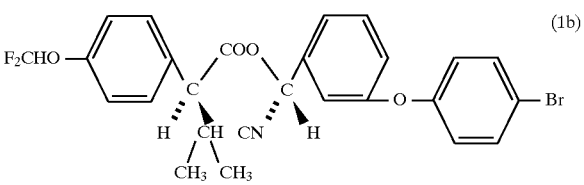

by:

(a) adding 1 mole of (S)-2-(4-difluoromethoxyphenyl)-3-methylbutyryl chloride to a mixture of 1 mole of 3-(4-bromophenoxy)benzaldehyde, 1 to 3 moles of aqueous NaCN and 1 to 5 times by weight organic solvent, (b) reacting the mixture of step 3(a) at −20° C. to the reflux temperature of the solvent in the mixture of step 3(a) for 0.1 to 100 hours, and (c) separating compounds Ia and Ib from the mixture of step 3(b); and 4. preparing compound Ia by:

(a) dissolving the mixture of compounds Ia and Ib obtained in step 3(c) in 1 to 5 times by weight of a solvent selected from the group consisting of a lower molecular weight alcohol, an aliphatic hydrocarbon, a ketone, and mixtures thereof, (b) adding the solution of step 4(a) to 0.01 to 3 moles of a base, (c) reacting the mixture of step 4(b) at −40° C. to 50° C. for 1 to 100 hours, and (d) collecting the precipitate by filtration to give compound Ia;

(b) Compound (Ia) is added to a mixture of 0.01–3 moles of base and alcohol, said base selected from the group consisting of triethylamine, pyridine, sodium carbonate, and sodium bicarbonate, while said alcohol is selected from the group consisting of methanol, ethanol, and isopropanol; after the dissolution is completed, stir the mixture at −40° C.—reflux temperature for 1–100 hrs.; and collect the precipitates by filtration to give a racemic mixture consisting essentially of the compound of formula Ia and the compound of formula Id.

* * * * *